(12) United States Patent
Tokumoto et al.

(10) Patent No.: US 7,883,504 B2
(45) Date of Patent: Feb. 8, 2011

(54) DEVICE FOR PERCUTANEOUS ABSORPTION PREPARATION

(75) Inventors: Seiji Tokumoto, Tsukuba (JP); Hirotoshi Adachi, Tsukuba (JP); Yasushi Fuchita, Tokyo (JP); Tatsuya Ogawa, Tokyo (JP); Hitoshi Otomo, Tokyo (JP)

(73) Assignees: Hisamitsu Pharmaceutical Co., Inc., Tosu-shi (JP); Kyodo Printing Co., Ltd., Tokyo (JP)

( * ) Notice: Subject to any disclaimer, the term of this patent is extended or adjusted under 35 U.S.C. 154(b) by 0 days.

(21) Appl. No.: 12/441,842

(22) PCT Filed: Aug. 31, 2007

(86) PCT No.: PCT/JP2007/066974

§ 371 (c)(1),
(2), (4) Date: Jun. 29, 2009

(87) PCT Pub. No.: WO2008/035558

PCT Pub. Date: Mar. 27, 2008

(65) Prior Publication Data

US 2010/0022942 A1    Jan. 28, 2010

(30) Foreign Application Priority Data

Sep. 19, 2006    (JP) .............................. 2006-252013

(51) Int. Cl.
*A61K 9/22*    (2006.01)

(52) U.S. Cl. ................ 604/890.1; 604/20; 604/181; 604/289; 604/306; 604/520; 424/449; 222/541.2

(58) Field of Classification Search .................. 604/20, 604/520, 82, 83, 85–87, 181–183, 185, 256, 604/289, 304–307, 890.1, 892.1, 288.01, 604/288.04; 222/80, 81, 83, 85, 153.01, 222/153.05, 153.06, 541.1–541.4; 424/446, 424/447, 449; 401/134
See application file for complete search history.

(56) References Cited

U.S. PATENT DOCUMENTS 4,741,437 A * 5/1988 Gorski et al. ................ 206/222

(Continued)

FOREIGN PATENT DOCUMENTS

EP    1 790 375 A1    5/2007

(Continued)

*Primary Examiner*—Kevin C Sirmons
*Assistant Examiner*—Bhisma Mehta
(74) *Attorney, Agent, or Firm*—Birch, Stewart, Kolasch & Birch, LLP

(57) ABSTRACT

The invention provides a device for a percutaneous absorption preparation, provided with a solution storage container which can exhibit good solution migration independently of the level of force. The device for a percutaneous absorption preparation comprises an electrode film comprising a base member (1) and an electrode layer (2) and having a dissolution liquid passage hole (9), a drug impregnation member (3) mounted on the electrode layer (2) side of the electrode film, and a dissolution liquid storage container (5) bonded to the base member (1) side of the electrode film via a lid member (7) covering the solution passage hole (9). The dissolution liquid storage container (5) comprises a bottom and a sidewall. A protrusion (5b) which faces the dissolution liquid passage hole (9) is provided at the center of the bottom, and the sidewall is provided with a vertically folded part (5c).

14 Claims, 17 Drawing Sheets

U.S. PATENT DOCUMENTS

| | | |
|---|---|---|
| 4,842,577 A | 6/1989 | Konno et al. |
| 2006/0142706 A1 | 6/2006 | Roy et al. |

FOREIGN PATENT DOCUMENTS

| | | |
|---|---|---|
| JP | 5-84180 B2 | 12/1993 |
| JP | 7-507464 A | 8/1995 |
| WO | WO-93/24177 A1 | 12/1993 |
| WO | WO-2004/105864 A1 | 12/2004 |
| WO | WO-2006/016647 A1 | 2/2006 |

\* cited by examiner

[Fig. 1]
(a) 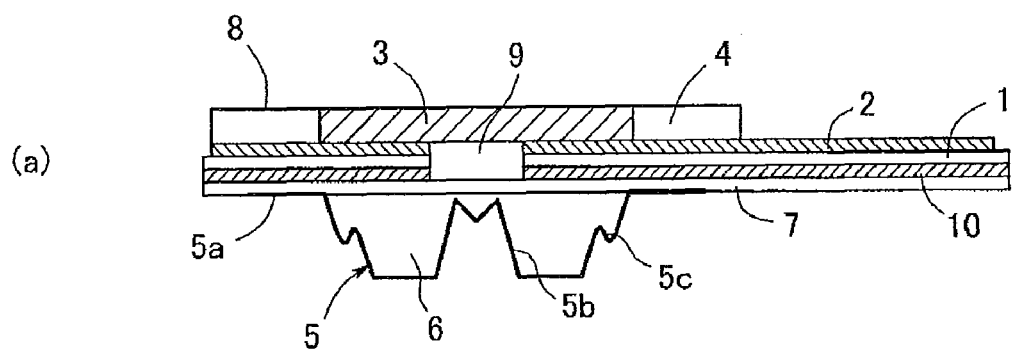
(b) 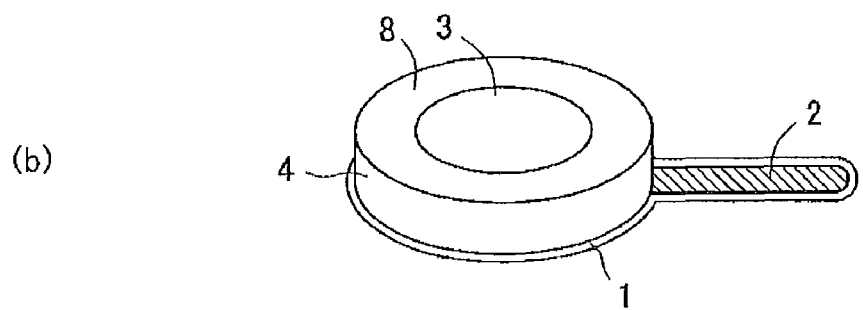

[Fig. 2]
(a)
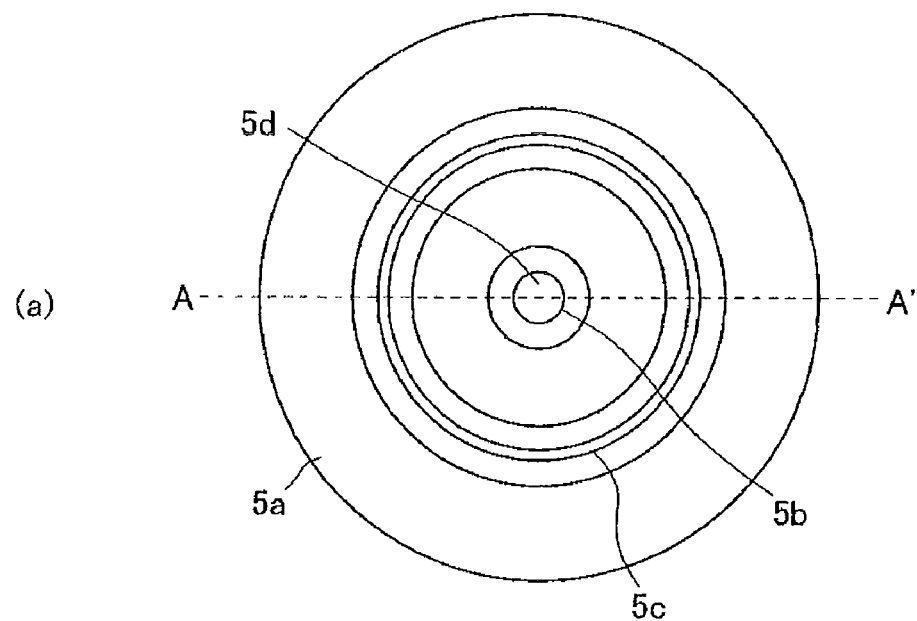
(b)
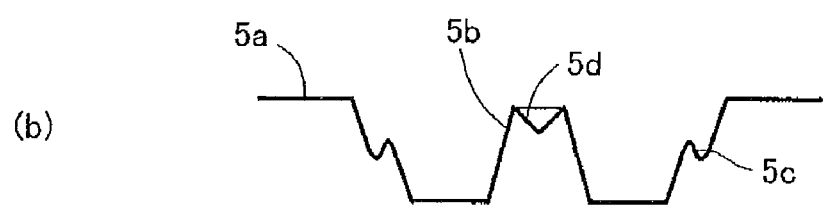

[Fig. 3]
(a)
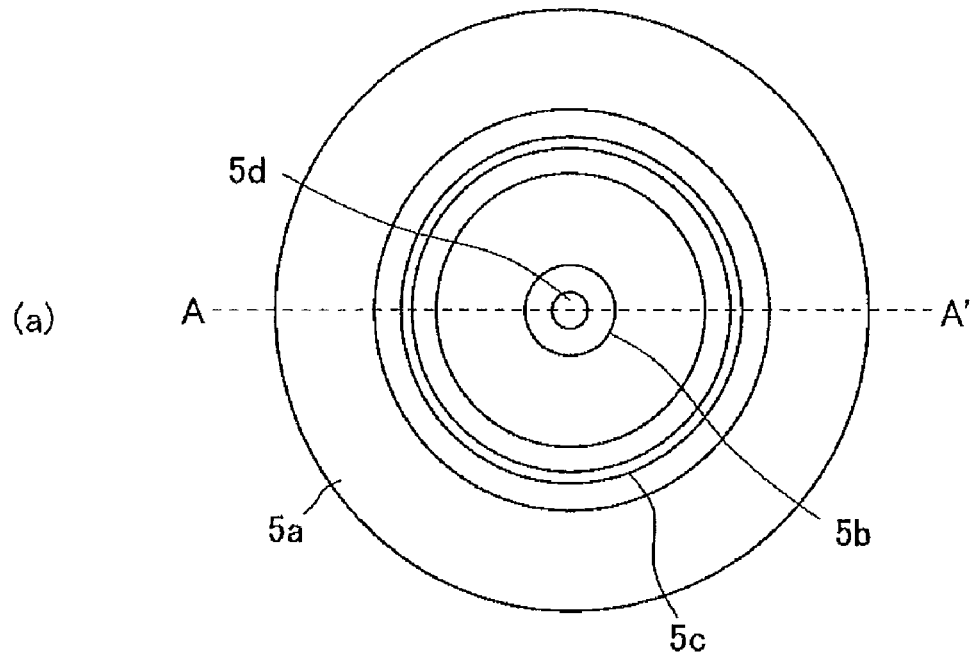
(b)
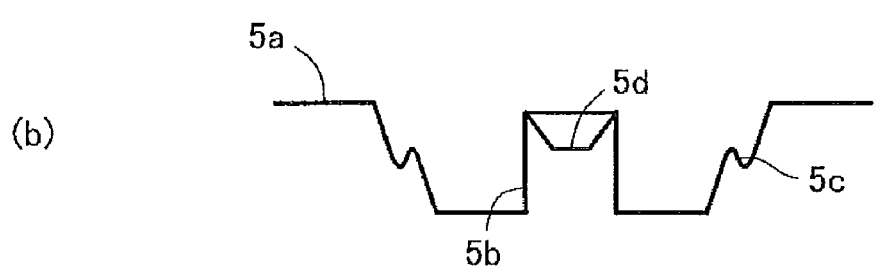

[Fig. 4]
(a)
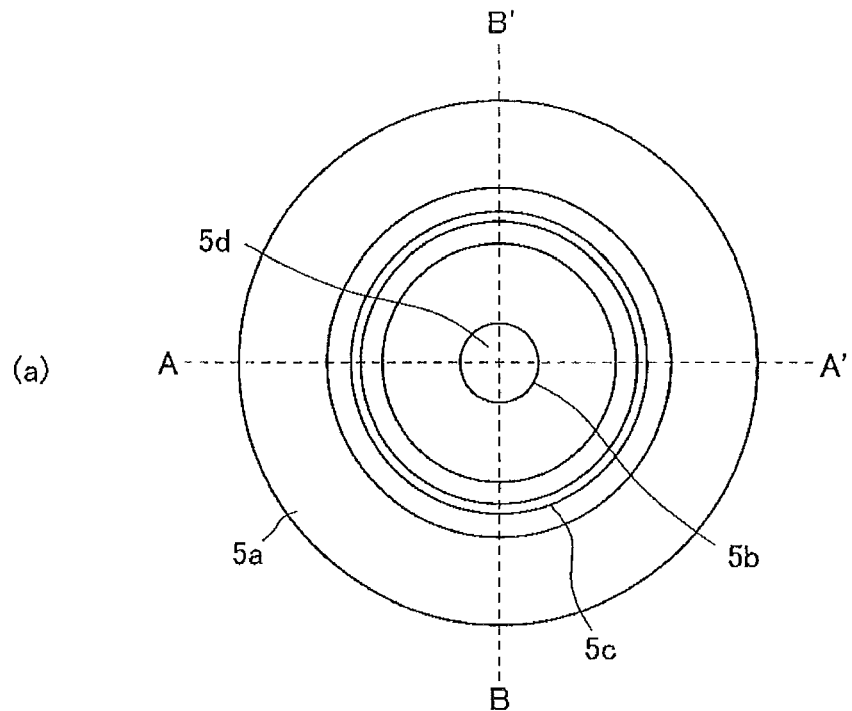
(b)
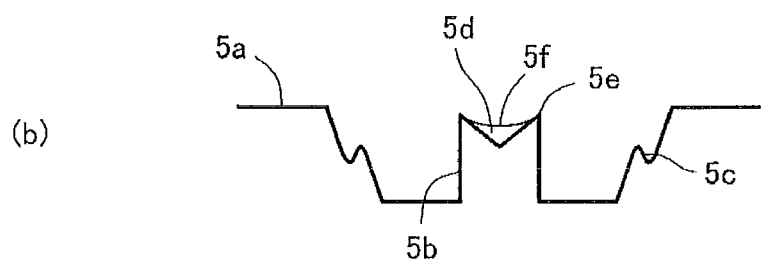
(c)
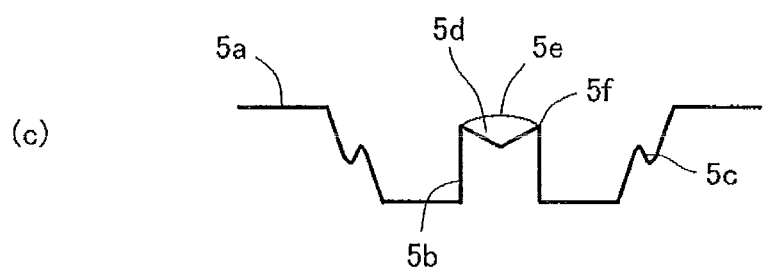

[Fig. 5]
(a)
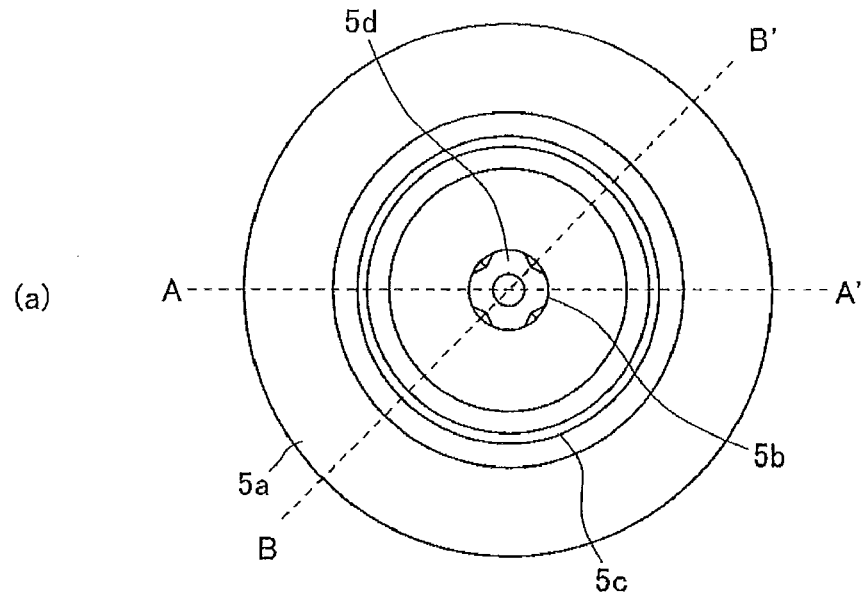
(b)
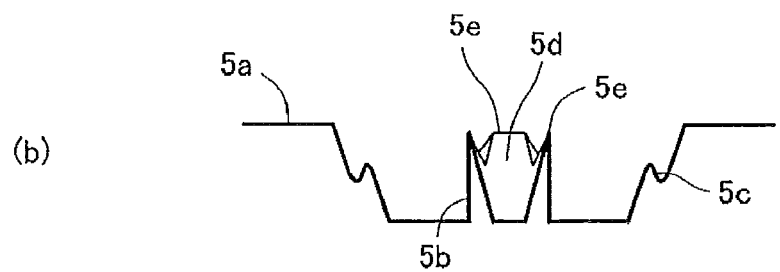
(c)
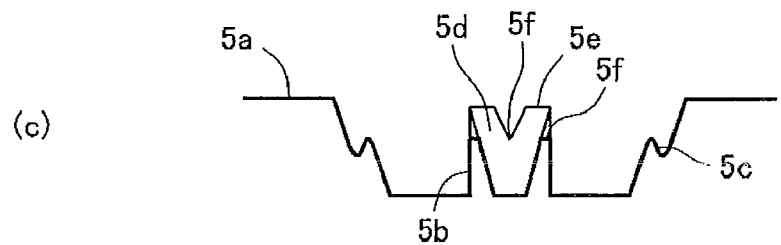

[Fig. 6]
(a)
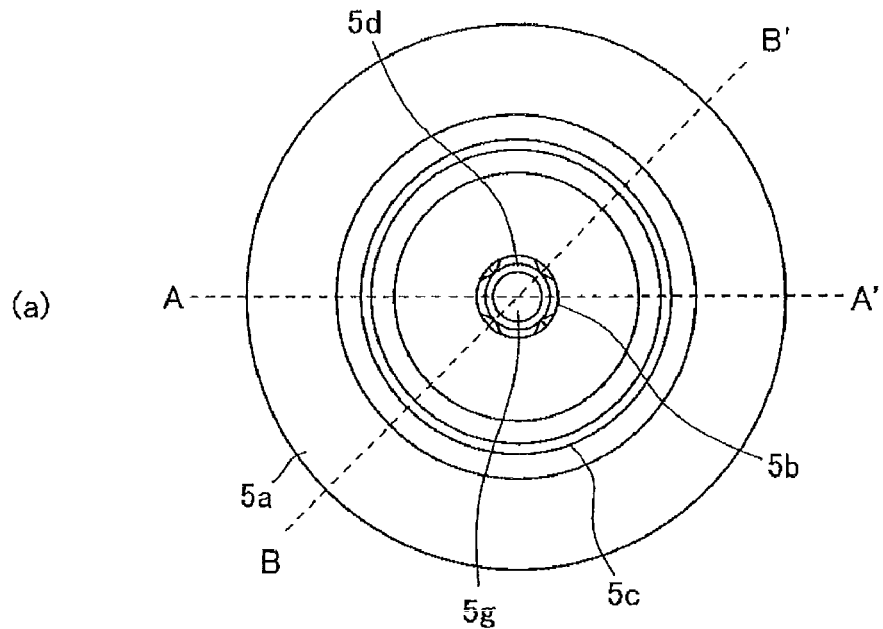
(b)
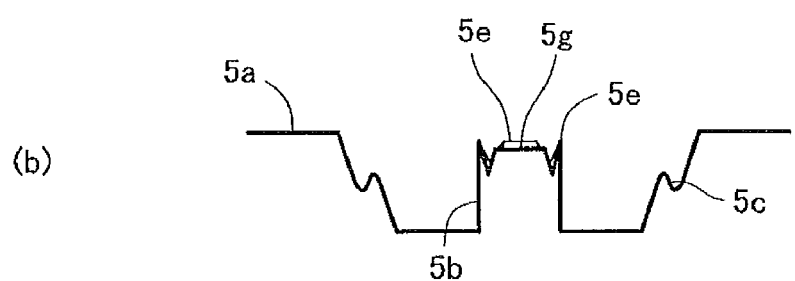
(c)
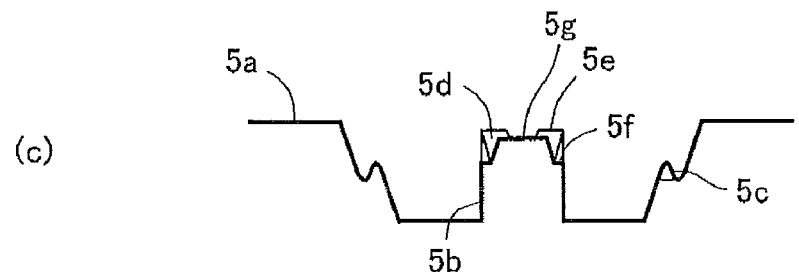

[Fig. 7]
(a)
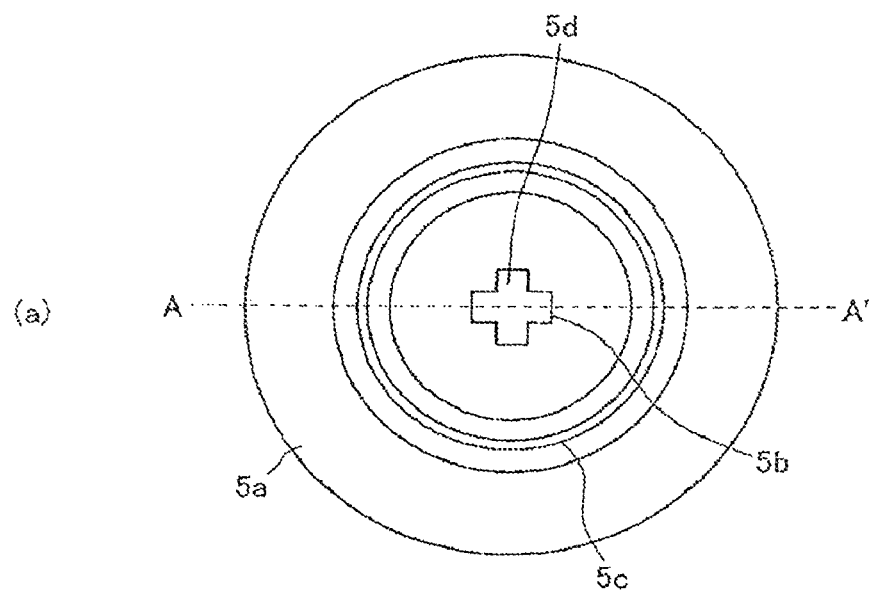
(b)
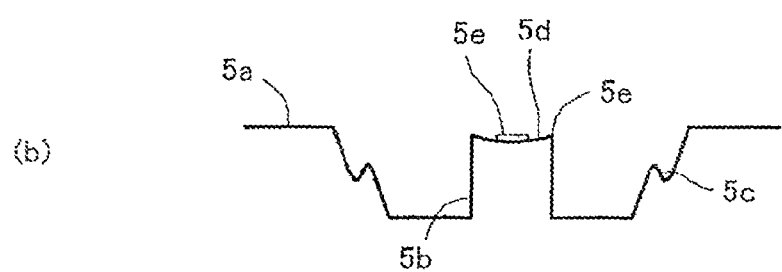
[Fig. 8]
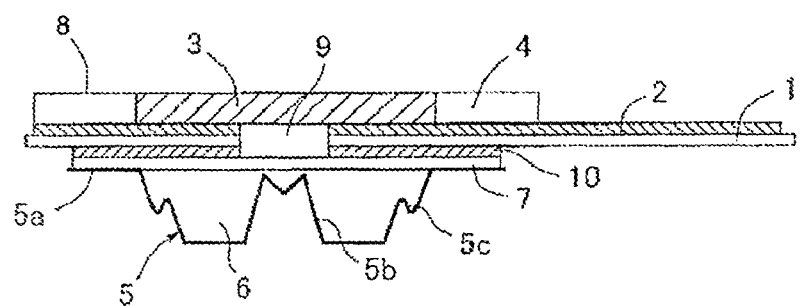

[Fig. 9]
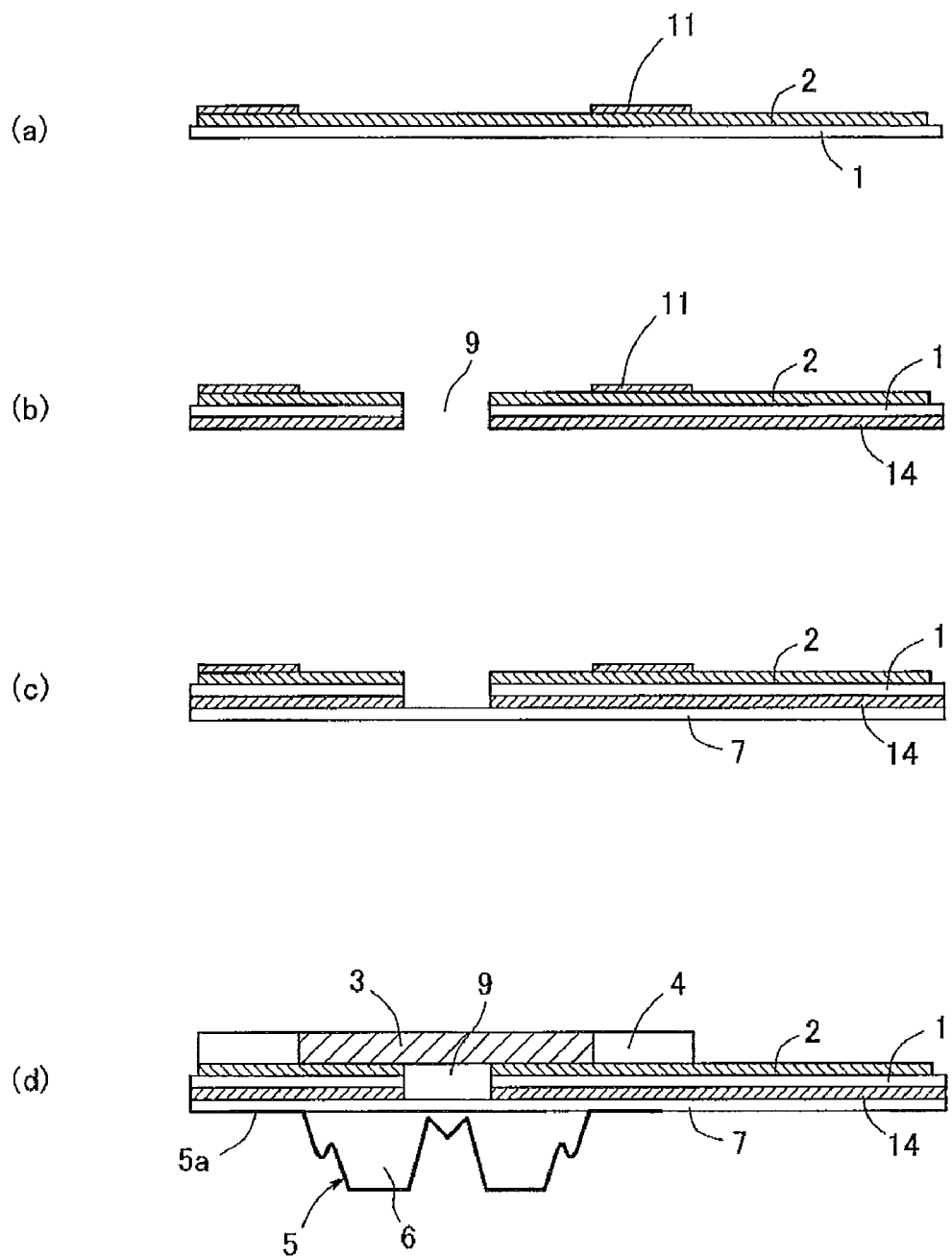

[Fig. 10]
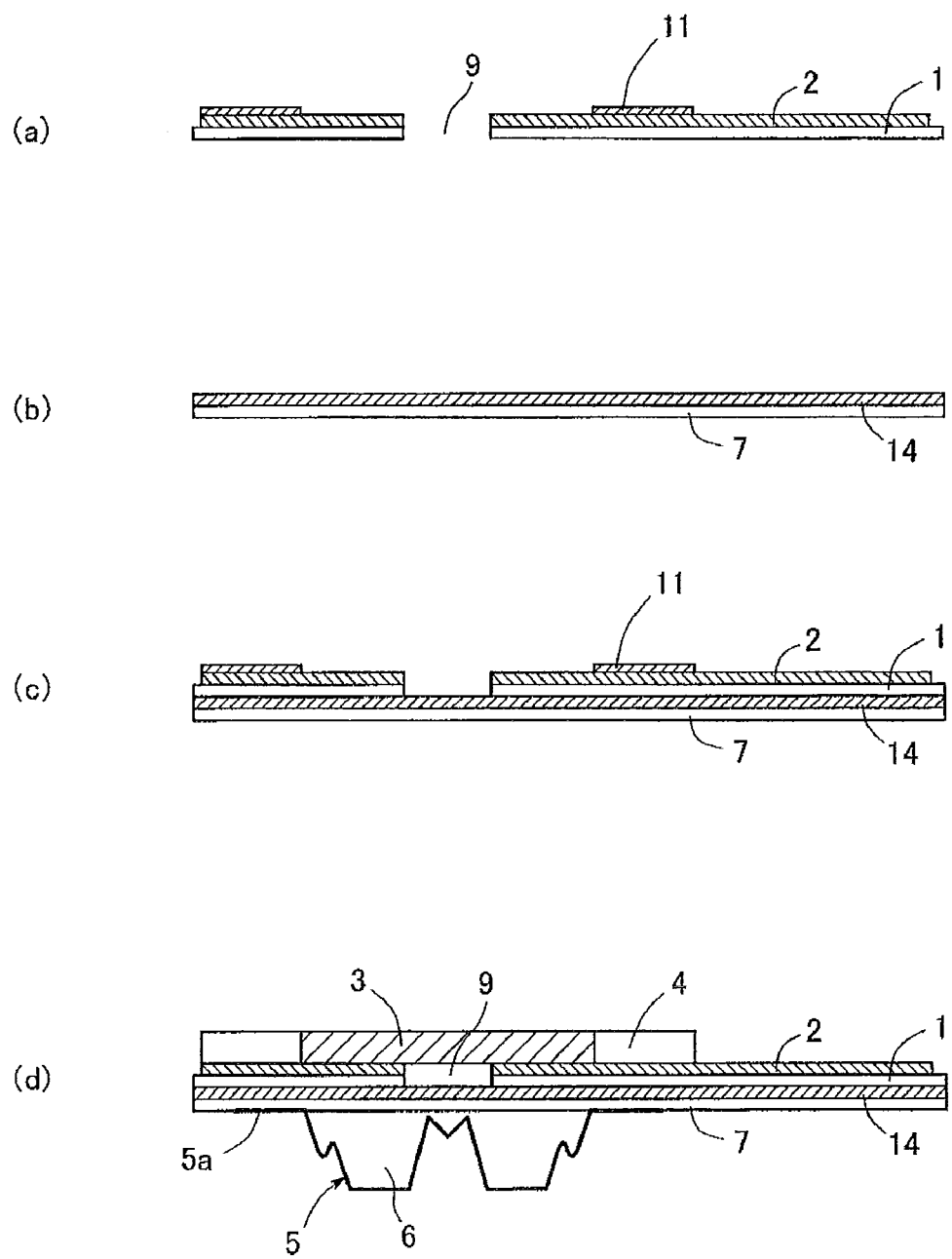

[Fig. 1 1]
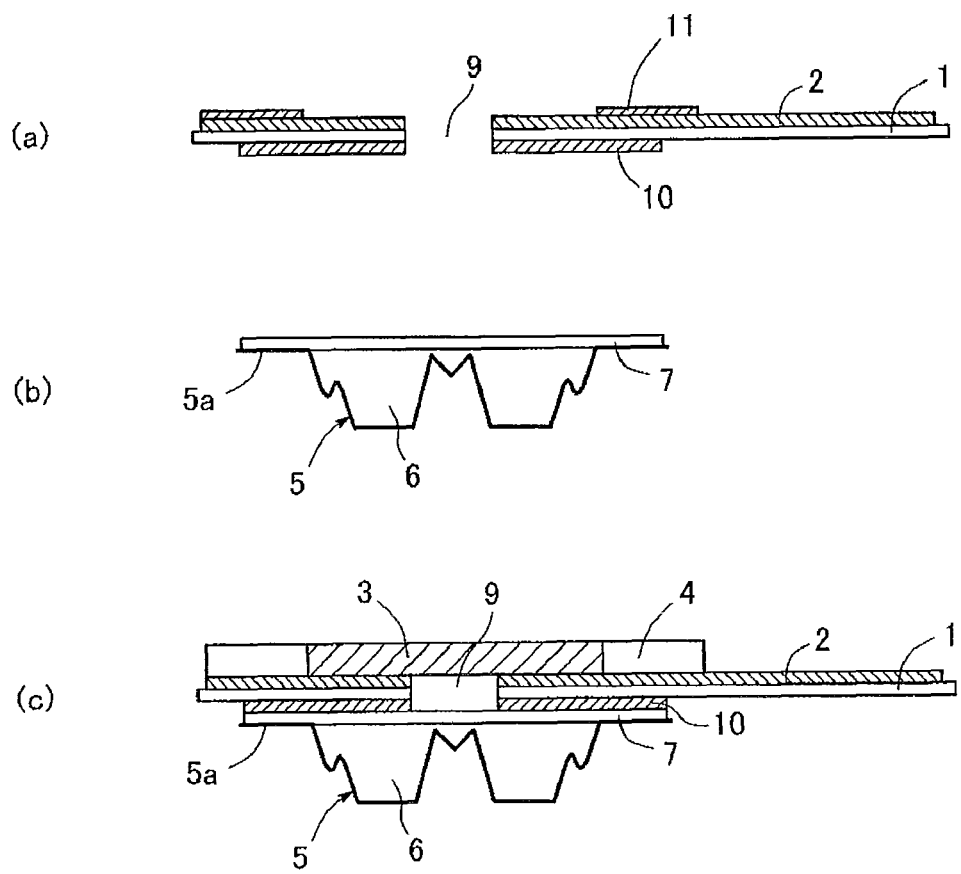

[Fig. 1 2]
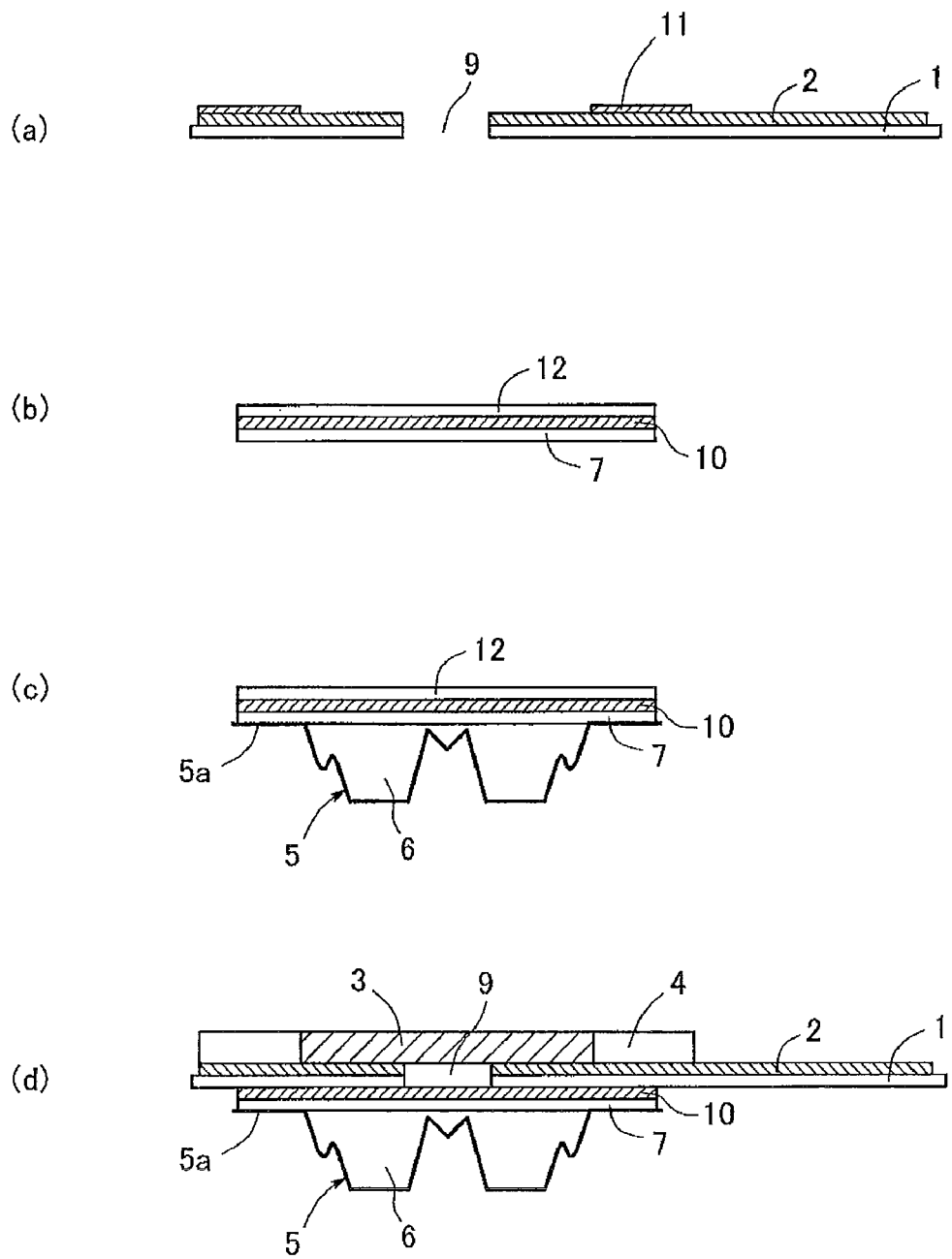

[Fig. 1 3]
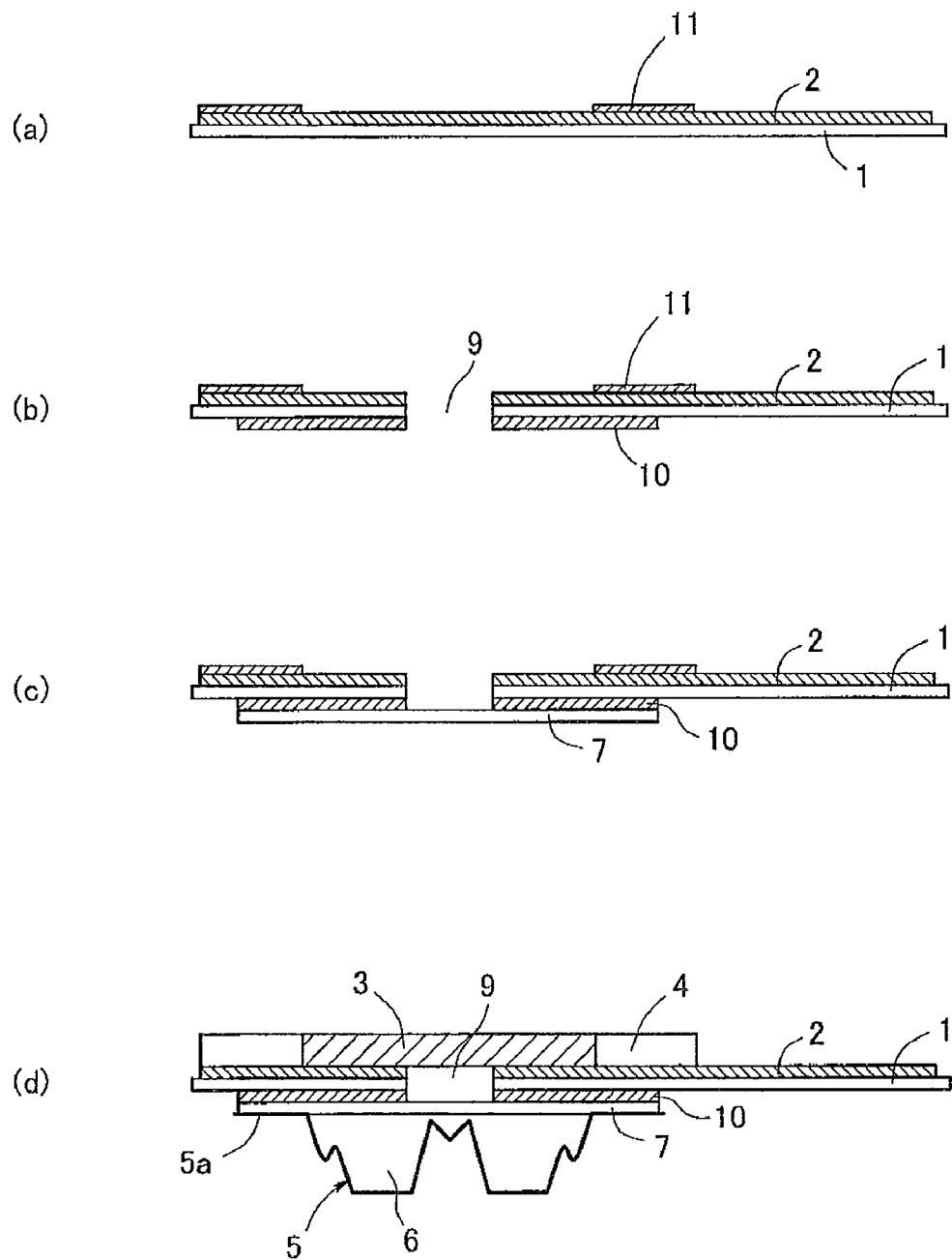

[Fig. 14]
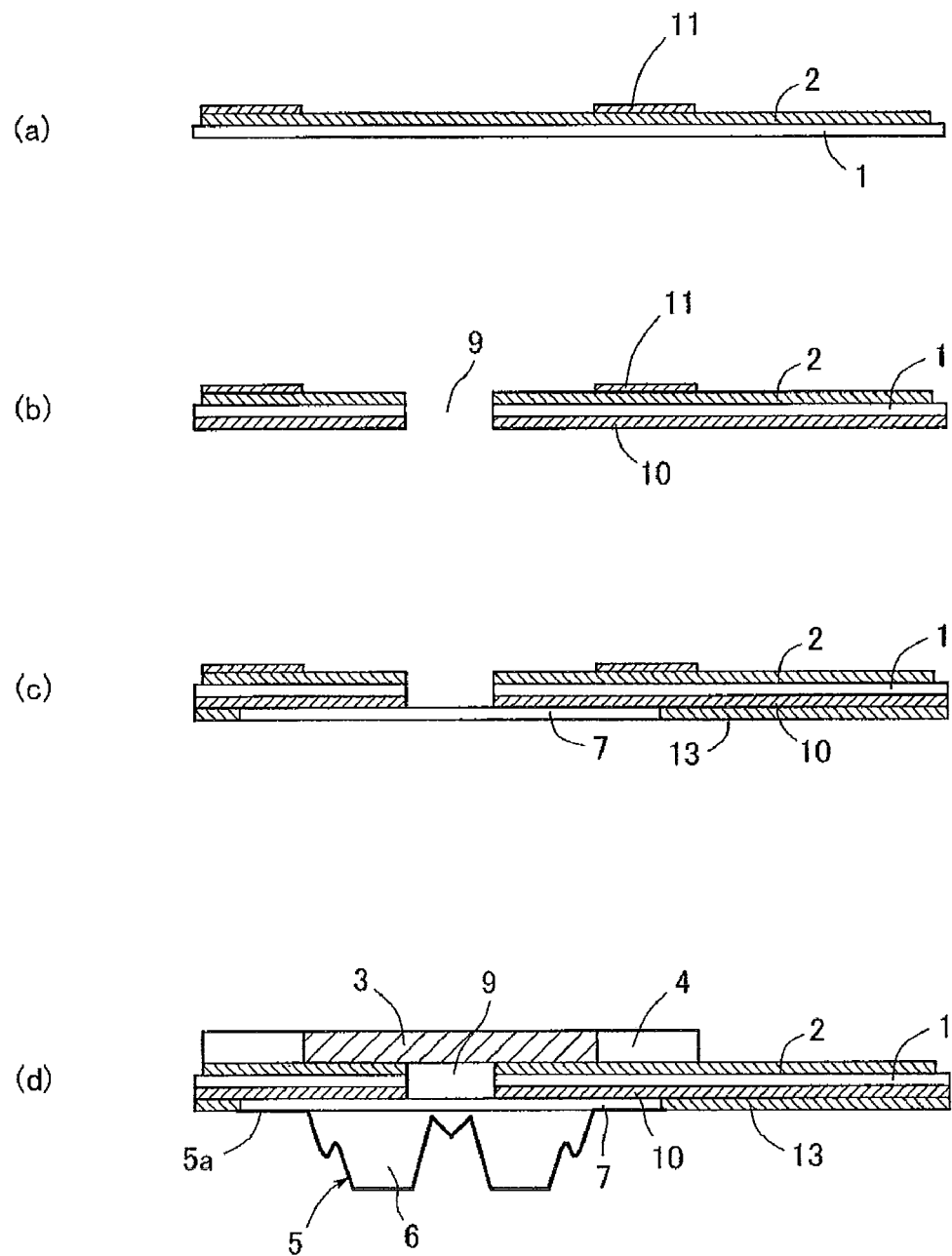

[Fig. 1 5]
(a)
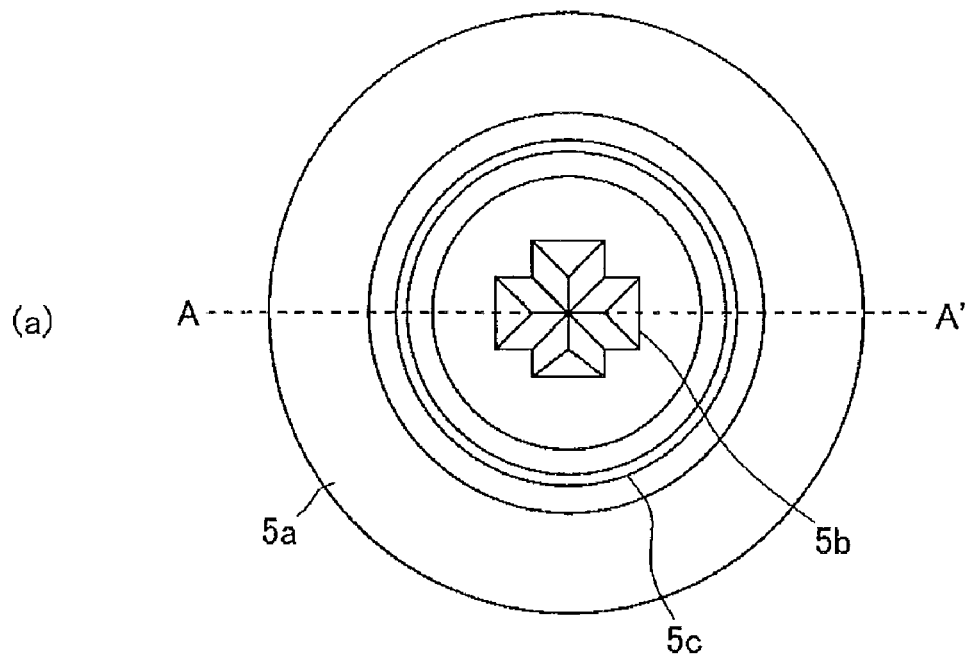
(b)
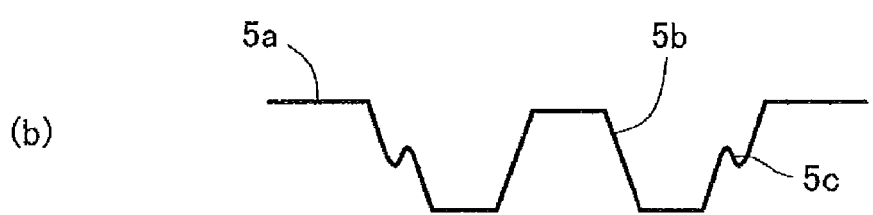

[Fig. 1 6]
(a)
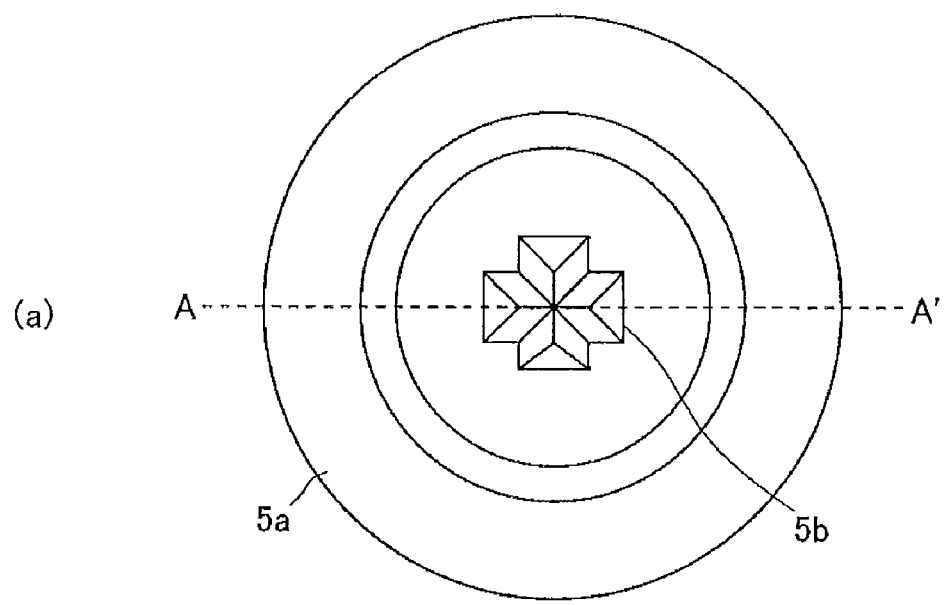
(b)
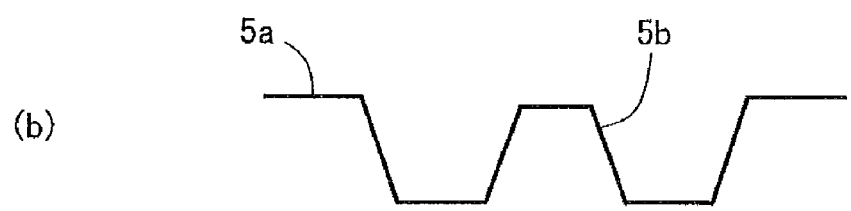

[Fig. 17]
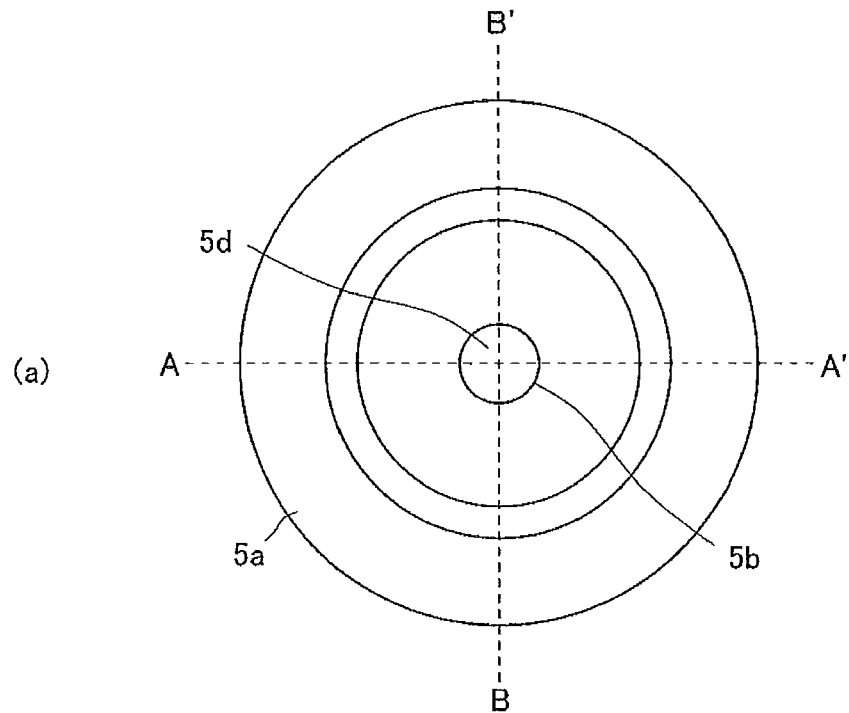
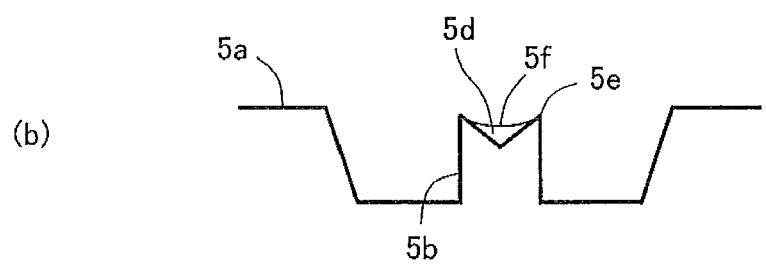
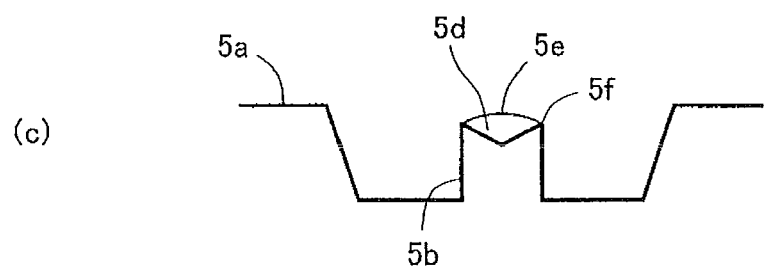

[Fig. 1 8]
(a)
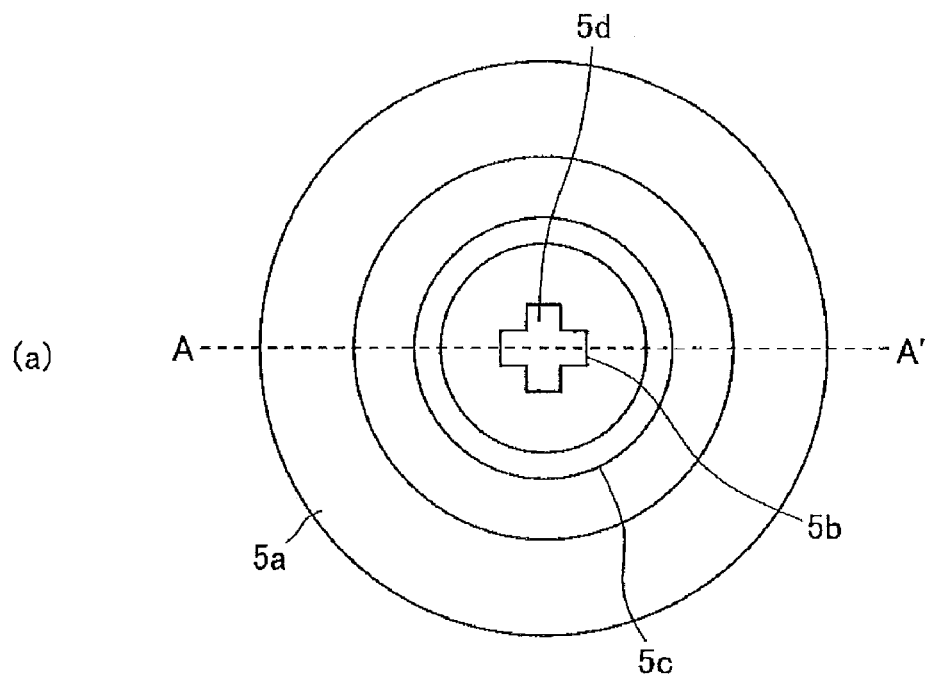
(b)
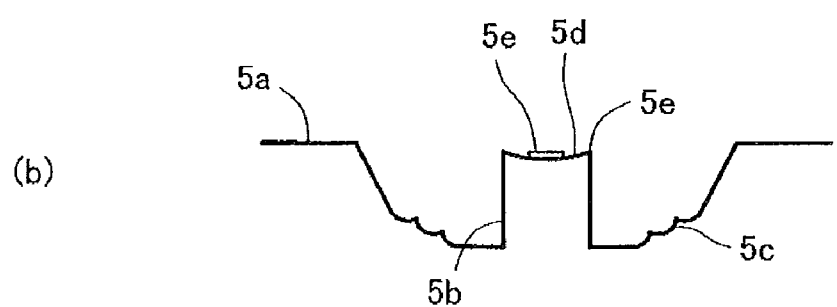

DEVICE FOR PERCUTANEOUS ABSORPTION PREPARATION

TECHNICAL FIELD

The present invention relates to a device for a percutaneous absorption preparation used in the medical field of treatment or diagnosis.

BACKGROUND ART

The device for a percutaneous absorption preparation is a device which causes to absorb a drug through the skin or the mucosa, and one of it is an iontophoresis device. The iontophoresis device applies voltage to the skin or the mucosa and electrically migrates the drug to administer the drug through the skin or the mucosa.

In a case where a drug which is particularly poor in stability to water is used in the iontophoresis device, it is necessary to store separately the drug and a dissolution liquid from each other in order to prevent the drug from being deteriorated during its storage and to mix the drug and the dissolution liquid immediately before the use for treatment. For that, it is convenient to have a structure that a dissolution liquid storage container is integrated with an iontophoresis electrode itself which includes an electrode layer to be applied to the skin or the mucosa, and the dissolution liquid and the drug can be mixed by a simple operation.

For example, Patent Literature 1 proposes a structure that a capsule in which an electrolyte solution is encapsulated is fitted to a plaster structure for iontophoresis which is composed of an electrode layer and a drug-containing layer with an aluminum foil between them. According to this structure, the capsule is pushed to break a film such as the aluminum foil or the like by a projection formed on the capsule so to migrate the contained electrolyte toward the drug-containing layer, thereby mixing the electrolyte and the drug.

Patent Literature 1: Japanese Patent Publication No. 5-84180

SUMMARY OF THE INVENTION

Problems to be Solved by the Invention

But, the device described in Patent Literature 1 has a problem that if a force of pushing the capsule to migrate the contained electrolyte toward the drug-containing layer is insufficient, the electrolyte is not sufficiently migrated to the drug-containing layer.

The present invention solves the above problem and provides a device for a percutaneous absorption preparation provided with a dissolution liquid storage container which can exhibit good migration of the dissolution liquid independent of the strength of force.

Means for Solving the Problems

The present invention configured to remedy the above-described problem has the following structures.

A device for a percutaneous absorption preparation is comprised of a holder having a dissolution liquid passage hole, a drug impregnation member formed on one surface side of the holder, and a dissolution liquid storage container provided on the other surface side of the holder with a lid member covering the dissolution liquid passage hole between the holder and the dissolution liquid storage container wherein the dissolution liquid storage container has a bottom, a sidewall and a protrusion formed at the center of the bottom to face the dissolution liquid passage hole, and the sidewall has a vertically folded part.

The invention includes the following structure as a preferable embodiment.

The protrusion formed at the center of the bottom of the storage container has a recessed portion at its tip for rupturing the lid member. Specially, the protrusion has a top and a bottom on its outer circumference. The top and the bottom each are provided in plural and arranged symmetrically to one another on the outer circumference of the protrusion.

The iontophoresis device has the holder formed with an electrode layer formed on a base member, and the base member is bonded to the lid member. The lid member is a resin lid member and bonded to the base member with a thermoplastic resin layer or an adhesive layer between them. Especially, the resin lid member surface positioned at the solution passage hole does not have the thermoplastic resin layer or the adhesive layer. The lid member is an aluminum lid member, the dissolution liquid storage container has a flange portion around its opening, and the aluminum lid member is arranged within the outer diameter of the flange portion of the dissolution liquid storage container. And, the aluminum lid member and the base member are mutually bonded with the adhesive layer between them. Especially, the aluminum lid member surface positioned at the solution passage hole does not have the adhesive layer. The aluminum lid member and the dissolution liquid storage container are mutually bonded with a sealant layer between them.

EFFECTS OF THE INVENTION

The invention provides a device for a percutaneous absorption preparation which has a folded part formed on the sidewall of the dissolution liquid storage container, so that its operability to migrate the dissolution liquid is improved, a high migration rate of the dissolution liquid can be obtained stably regardless of a level of force to push the container, and it is conveniently used.

Especially, according to the invention, a recessed portion is formed on the tip of the protrusion formed on the bottom of the dissolution liquid storage container, so that when the dissolution liquid storage container is pushed, the initial contact between the protrusion and the lid member can be made not a plane contact but a line contact, the lid member can be subjected to initial rupture effectively by a stress concentration on it, and the lid member can be broken through along a large area corresponding to the contour of the protrusion. In other words, the lid member can be broken through along a large range without fail, so that a dissolution liquid migration rate can be increased, and a desired drug efficacy can be realized.

In a case where the outer circumference of the protrusion is provided with a top and a bottom, the initial contact between the protrusion and the lid member can be changed from a line contact state to approximately a point contact state, and the lid member can be broken through more effectively.

And, in a case where the top and the bottom are respectively provided in plural and arranged symmetrically on the outer circumference of the protrusion, the lid member can be subjected to initial rupture equally at the plural portions, and the lid member can be broken through along a large range more securely.

When the resin lid member is used according to the invention, there is no possibility of causing a leakage of electricity when current is applied, and reliability and safety become excellent.

When the aluminum lid member is used according to the invention, the lid member is not exposed to the device surface, so that there is no possibility of causing a leakage of electricity when current is applied, and reliability and safety become excellent.

The device for a percutaneous absorption preparation of the invention excelling in reliability and safety can be mass-produced easily, and the holder having the lid member bonded to the base member can be mass-produced by using a material such as a rolled sheet or the like.

BRIEF DESCRIPTION OF THE DRAWINGS

FIG. 1 is a schematic diagram showing a structure example of the iontophoresis device according to a preferable embodiment of the invention.

FIG. 2 is a schematic diagram showing a dissolution liquid storage container of the iontophoresis device shown in FIG. 1.

FIG. 3 is a schematic diagram showing another structure example of the dissolution liquid storage container used in the invention.

FIG. 4 is a schematic diagram showing another structure example of the dissolution liquid storage container used in the invention.

FIG. 5 is a schematic diagram showing another structure example of the dissolution liquid storage container used in the invention.

FIG. 6 is a schematic diagram showing another structure example of the dissolution liquid storage container used in the invention.

FIG. 7 is a schematic diagram showing another structure example of the dissolution liquid storage container used in the invention.

FIG. 8 is a schematic diagram showing a structure example of an iontophoresis device using an aluminum lid member in the invention.

FIG. 9 is a manufacturing process chart showing an example of a device for a percutaneous absorption preparation of the invention.

FIG. 10 is a manufacturing process chart showing an example of a device for a percutaneous absorption preparation of the invention.

FIG. 11 is a manufacturing process chart showing an example of a device for a percutaneous absorption preparation of the invention.

FIG. 12 is a manufacturing process chart showing an example of a device for a percutaneous absorption preparation of the invention.

FIG. 13 is a manufacturing process chart showing an example of a device for a percutaneous absorption preparation of the invention.

FIG. 14 is a manufacturing process chart showing an example of a device for a percutaneous absorption preparation of the invention.

FIG. 15 is a schematic diagram showing a dissolution liquid storage container used in an example of the invention.

FIG. 16 is a schematic diagram showing a dissolution liquid storage container used as Comparative Example 1 in the example of the invention.

FIG. 17 is a schematic diagram showing a dissolution liquid storage container used as Comparative Example 2 in the example of the invention.

FIG. 18 is a schematic diagram showing another structure example of the dissolution liquid storage container used in the invention.

EXPLANATION OF REFERENCE NUMERALS

1: Base member
2: Electrode layer
3: Drug impregnation member
4: Expanded sheet
5: Dissolution liquid storage container (dissolution liquid storage blister container)
5a: Flange portion
5b: Protrusion
5c: Folded part
5d: Recessed portion
5e: Top
5f: Bottom
5g: Second protrusion
6: Dissolution liquid
7: Lid member
8: Adhesive
9: Dissolution liquid passage hole
10: Adhesive layer
11: Sealing layer
12: Release film
13: Coating film
14: Thermoplastic resin layer

MODE FOR CARRYING OUT THE INVENTION

Referring to the drawings, embodiments of the invention are described taking as examples the iontophoresis devices to which the invention is preferably applied.

FIG. 1 is a diagram showing an example of the iontophoresis device according to one embodiment of the invention, (a) is a sectional view, and (b) is a perspective view. The iontophoresis device of this example is mainly comprised of a base member 1 formed of a polyethylene terephthalate (PET) film or the like, an electrode layer 2 formed on the base member 1, a drug impregnation member 3 formed on the electrode layer 2, an expanded sheet 4 formed on the circumference of the drug impregnation member 3, a dissolution liquid storage container (dissolution liquid storage blister container) 5 in which a dissolution liquid 6 is charged, and a lid member 7 which functions as a lid member of the dissolution liquid storage container 5.

(Holder)

To configure the iontophoresis device according to the invention, the holder is an electrode film comprising the base member 1 and the electrode layer 2. When the device does not have the electrode layer 2, the base member 1 alone is used as the holder.

As the base member 1, there are, for example, plastic films of polyethylene terephthalate (PET), polyimide, polyamide, polypropylene and the like, and the polyethylene terephthalate is particularly suitably used because it is excellent in insulation properties, heat resistance, machinability and the like. And, such films may be used as a single film or a composite film.

The electrode layer 2 is composed of a substantially circular part which becomes an electrode discharge portion and an extended part which becomes an electrode terminal portion. As a material for the electrode layer 2, for example, materials based on metal and nonmetal conductive materials such as silver, silver chloride, carbon, titanium, platinum, gold, aluminum, iron, nickel and a mixture of them can be used. A conductive paste based on such a material may also be used. Such a conductive paste can be used to form the electrode layer 2 by screen printing suitable for mass production.

To move the dissolution liquid 6 in the dissolution liquid storage container 5 to the drug impregnation member 3 at the time of use, a dissolution liquid passage hole 9 is formed in the holder having the electrode layer 2, which is formed on the base member 1, by punching fabrication.

(Drug Impregnation Member)

The material for the drug impregnation member 3 is not limited to a particular one if it is a hydrophilic base member and can absorb and hold a drug solution, and may be a cellulose fiber, a rayon fiber, a nylon fiber, a polyurethane foam, a polycarbonate foam, a polyvinyl alcohol foam, a polyester foam, a polyester nonwoven fabric, cotton or a composite of them.

(Expanded Sheet)

The expanded sheet 4 has a function to prevent the drug solution from externally leaking out of the device when the drug impregnation member 3 is impregnated with the dissolution liquid 6. Therefore, it is required to be securely adhered to the holder. Since the device is used in a state attached to the skin, it is a flexible soft foam and it is desirable to use as a substrate a foam of various types of polymers such as polyurethane, polyethylene, polyvinyl chloride, polychloroprene, acrylic resin and polystyrene. And, since it is attached to the skin when used, it is desirable to have a rubber-based, acrylic-based, silicone-based, polyvinyl-based, polyester-based or polyurethane-based adhesive 8 coated onto one side.

(Sealing Layer)

The drug impregnation member 3 and the expanded sheet 4 can be bonded to the holder with a sealing layer (not shown), which is formed of an adhesive material or a heat-sealable material, provided on a prescribed region such as a peripheral portion of the electrode layer 2 of the holder. The sealing layer is preferably heat sealable in view of an easy manufacturing process. The heat-sealable materials are polydiene, polyacryl, polymethacryl, acrylamide, polyvinyl alcohol, polyethylene, polyvinyl ester, polystyrene, polycarbonate, polyester, polyurethane, polysiloxane, polyamide, polyacetal and polyacrylonitrile. Preferably, they are polydiene, polyacryl, polymethacryl, polyethylene, polyvinyl ester, polystyrene, polyester and polysiloxane. More preferably, they are polydiene, polyacryl, polymethacryl, polyester and polysiloxane but not limited to them. The adhesive materials are those having acryl or silicone as the main component but not limited to them.

(Dissolution Liquid Storage Container)

FIG. 2 is a diagram showing the dissolution liquid storage container 5 of FIG. 1, (a) is a top view, and (b) is an A-A' sectional view of (a). As shown in FIG. 2, the dissolution liquid storage container 5 has a flange portion 5a on the outer circumference of the opening, a protrusion 5b is formed at the center of the bottom, and a vertically folded part 5c is formed on the sidewall. The bottom and the sidewall form a recessed portion for storing the dissolution liquid 6. The flange portion 5a extends from the sidewall and is disposed on the holder. The protrusion 5b is within the recessed portion so as to face the dissolution liquid passage hole 9. The vertically folded part 5c of the sidewall is disposed at a middle part of the sidewall and is between the bottom and the flange portion 5a. The vertically folded part 5c is circumferentially disposed at the middle part of the sidewall and is between the bottom and the flange portion 5a.

At the time of using the device for a percutaneous absorption preparation of the invention, the device is applied to the skin with the adhesive 8 provided on the top surface of the expanded sheet 4, the bottom of the dissolution liquid storage container 5 is pushed to break the lid member 7 by the protrusion 5b to migrate the dissolution liquid 6 to the drug impregnation member 3 through the dissolution liquid passage hole 9 to mix with the drug. And, a current is passed to the electrode layer 2 to ionize the drug solution to introduce it into the body through the skin. If the lid member 7 could not be broken sufficiently at this time, the dissolution liquid 6 is not migrated satisfactorily to the drug impregnation member 3 but partially remained in the dissolution liquid storage container 5, and a desired drug efficacy cannot be expected.

According to the invention, since the vertically folded part 5c is formed on the sidewall of the dissolution liquid storage container 5, the sidewall is readily folded inward at the folded part 5c when the bottom is pushed to break the lid member 7 by the protrusion 5b. Even if the force of pushing the bottom of the container 5 is weak, it is possible to break through the lid member 7 by pushing the protrusion 5b against it, and the dissolution liquid 6 can be migrated sufficiently to the drug impregnation member 3.

As exemplified in FIG. 2, the folded part 5c according to the invention has a shape that the sidewall has a cross section of a shape folded in a vertical direction, and its folded length and the width of the folded part 5c are not particularly restricted if the dissolution liquid 6 is migrated well and stably.

According to the invention, a recessed portion 5d is formed on the tip of the protrusion 5b which is formed on the bottom of the dissolution liquid storage container 5, so that when the bottom of the dissolution liquid storage container 5 is pushed, the initial contact between the protrusion 5b and the lid member 7 can be made not a plane contact but a line contact, the lid member 7 can be subjected to initial rupture effectively by the stress concentration on it, and the lid member 7 can be broken through along a large area corresponding to the contour (namely, the contour of the recessed portion 5d) of the tip of the protrusion 5b.

The lid member 7 which seals the flange portion 5a of the dissolution liquid storage container 5 comes to have a taut state toward the flange portion 5a but becomes loose at the center. Therefore, it is easily broken at a portion closer to the outer circumference than at the center. Thus, the recessed portion 5d is formed on the tip of the protrusion 5b as exemplified in FIG. 2, and the initial breakage is caused at a portion away from the center of the lid member 7, so that the lid member can be broken quite easily and effectively.

Other examples of the dissolution liquid storage container 5 preferably used in the invention are shown in FIG. 3 through FIG. 7 and FIG. 18. Among them, (a) is a top view, (b) is an A-A' sectional view of (a), and (c) is a B-B' sectional view of (a).

The examples of FIG. 2 and FIG. 3 have the tip of the protrusion 5b formed to have the same height along the entire circumference, but as exemplified in FIG. 4 through FIG. 6, the outer circumference (or an outer circumference of the recessed portion 5d) of the protrusion 5b may be preferably formed at a top 5e and a bottom 5f. By adopting such a form, the initial contact between the protrusion 5b and the lid member 7 can be further changed from the line contact state to a point contact state, and the stress can be further concentrated to break through the lid member 7 more effectively. As exemplified in FIG. 4 through FIG. 6, the top 5e and the bottom 5f each are provided in plural and arranged symmetrically on the outer circumference of the protrusion 5b, so that the lid member 7 can be subjected to initial rupture equally at the plural portions and can be broken through along a large range more securely.

In the example shown in FIG. 6, a second protrusion 5g lower than the top 5e is formed in the recessed portion 5d. By adopting such a style, even if the protrusion 5b is not pushed deep enough, the inner side of the lid member 7 which is undergone the initial rupture by the top 5e can be pushed by the second protrusion 5g to enlarge the opening, so that the insufficient broken state can be avoided effectively.

The contour of the protrusion 5b is not limited to the circular shape (cylindrical shape) exemplified in FIG. 2 through FIG. 6 but may have, for example, a polygonal columnar shape, a cross shape, or the like as exemplified in FIG. 7 and FIG. 18.

For the dissolution liquid storage container 5, it is desired to use a material having a high steam barrier property to prevent the dissolution liquid 6 from evaporating and decreasing its amount when the dissolution liquid 6 is charged and stored in it. Specifically, examples of such a material include polyvinyl chloride, polyvinylidene chloride, polyethylene, polypropylene, polystyrene, polyamide, polymethylmethacrylate, polycarbonate, polyester, polyvinyl alcohol, polyvinyl acetate, thermoplastic elastomer, cyclic olefine polymer, cyclic olefine copolymer, a copolymer of ethylene and an organic carboxylic acid derivative having an ethylenically unsaturated bond such as ethylene-methacrylate copolymer, ethylene-vinyl acetate copolymer, ethylene-acrylate copolymer or ethylene vinyl acetate-methyl methacrylate copolymer, a trifluoroethylene chloride resin, and a metallic foil such as aluminum. The dissolution liquid storage container 5 can be obtained by vacuum molding, compressed air molding or vacuum compressed air molding of a monolayer or laminated multilayer sheet.

(Lid Material)

The lid member 7 is preferably formed of a material excelling in a steam barrier property and a break-through characteristic such that permeation of moisture to the drug impregnation member 3 is prevented during storage and it is broken easily to mix the dissolution liquid 6 of the dissolution liquid storage container 5 and the drug of the drug impregnation member 3 when used. Specifically, resin or aluminum is preferably used for the lid member 7. And, a half-cut line may be formed in the lid member 7 to facilitate its rupture.

Example materials for the resin lid member used in the invention include polyolefin such as polypropylene, an ethylene-propylene copolymer, polyethylene and the like, polyester and polystyrene, and it is preferably a uniaxially-stretched sheet or a sheet with an inorganic filler of calcium carbonate or the like blended into the above material.

The resin lid member and the base member 1 are preferably bonded with a thermoplastic resin layer (14 in FIG. 9 described later) or an adhesive layer 10 between them.

As the thermoplastic resin, there can be used a sealant resin such as polypropylene based resins and polyethylene based resins such as low-density polyethylene, medium-density polyethylene, high-density polyethylene, linear low-density polyethylene, ethylene-vinyl acetate copolymer, ethylene-acrylic acid copolymer, ethylene-methacrylic acid copolymer, ethylene-ethylacrylate copolymer, ethylene-methylmethacrylate copolymer, ethylene-methacrylate copolymer, ionomer, and a derivative or mixture of them.

To bond via the thermoplastic resin layer, the thermoplastic resin is sandwiched and laminated between the base member 1 and the lid member 7. As a laminating method, various types of fabrication methods such as an extrusion laminating method, a dry laminating method, a thermal laminating method and the like can be used. The thermoplastic resin is laminated by extruding by a T die according to the extrusion laminating method, and laminated by forming a film by an inflation method or a T-die method according to the dry and heat lamination method. In a case where the base member 1 in which the dissolution liquid passage hole 9 is formed is laminated, the thermal laminating method is used because the extrusion laminating method and the dry laminating method cannot be applied.

To bond the adhesive layer 10, a rubber-based, acrylic-based, silicone-based, polyvinyl-based, polyester-based or polyurethane-based one is suitably used in view of safety and elimination of disadvantages involved at the time of moistening.

To bond the base member 1 and the resin lid member 7 via the adhesive layer 10, the lid member 7 may be sealed with the flange portion 5a of the dissolution liquid storage container 5 and then bonded to the adhesive layer 10 formed on the base member 1, or the base member 1 and the lid member 7 may be laminated in advance before the flange portion 5a of the dissolution liquid storage container 5 and the lid member 7 are sealed. It is desirable to laminate the base member 1 and the lid member 7 in advance, because a gap between the lid member 7 and the adhesive layer 10 is eliminated, and a loss of the dissolution liquid due to capillary action can be prevented effectively.

In a case where an aluminum lid member is used in the invention, the aluminum lid member which has a sealant resin for sealing the flange portion 5a of the dissolution liquid storage container 5 coated on an aluminum foil is used.

When the device of the invention is an iontophoresis device, application of current is essential, and if a conductive material such as an aluminum foil is used for the lid member 7, there is a possibility of a leakage of electricity. Therefore, when the aluminum lid member is used, it is important that the lid member 7 is arranged within the outer diameter of the flange portion 5a of the dissolution liquid storage container 5 as shown in FIG. 8. Thus, the lid member 7 is not exposed to the outside of the device, and a leakage of electricity can be prevented effectively.

Since the aluminum lid member 7 is not directly adhered to a plastic film of PET or the like which is suitably used as the base member 1, the present invention is desirable that the base member 1 and the aluminum lid member 7 are bonded via the adhesive layer 10. The adhesive to be used for the adhesive layer 10 is not particularly limited, but the same adhesive as when the resin lid member is used can be used.

To bond the base member 1 and the aluminum lid member 7 via the adhesive layer 10, the adhesive layer 10 formed on the base member 1 and the lid member 7 may be bonded after the lid member 7 is sealed with the flange portion 5a of the dissolution liquid storage container 5, or the flange portion 5a of the dissolution liquid storage container 5 and the lid member 7 may be sealed after the base member 1 and the lid member 7 are laminated in advance. It is desirable to laminate the base member 1 and the lid member 7 in advance, because a gap between the lid member 7 and the adhesive layer 10 is eliminated, and a loss of the dissolution liquid due to capillary action can be prevented effectively.

At the time of using the iontophoresis device configured as described above, the device is applied to the skin with the adhesive 8 provided on the top surface of the expanded sheet 4, the bottom of the dissolution liquid storage container 5 is pushed by a finger to break the lid member 7 by the protrusion 5b formed on the bottom of the dissolution liquid storage container 5 to migrate the dissolution liquid 6 to the drug impregnation member 3 through the dissolution liquid passage hole 9 to mix with the drug. And, a current is passed to the electrode layer 2 to ionize the drug solution to introduce it into the body through the skin.

It was described above that the iontophoresis device had the holder provided with the electrode layer 2, but the present invention may be a device not having the electrode layer 2, and the individual component members in that case are the same as those of the above-described iontophoresis device. But, when the aluminum lid member is used as the lid member 7, the lid member may be larger than the outer diameter of the flange portion 5a of the dissolution liquid storage container 5 and exposed to the outside of the device.

Referring to FIG. 9 through FIG. 15, the method for producing a device for a percutaneous absorption preparation of the invention is described specifically taking as examples the iontophoresis devices exemplified in FIG. 1 and FIG. 8.

Manufacturing Example 1

FIG. 9 shows a manufacturing process chart of the iontophoresis device having the structure exemplified in FIG. 1.

The manufacturing method of this example 1 has a step of laminating the thermoplastic resin layer 14 on the entire surface of the electrode film, which has the electrode layer 2 formed on the base member 1, on the side bonded with the dissolution liquid storage container 5, a step of forming the dissolution liquid passage hole 9 in the electrode film having laminated the thermoplastic resin layer 14, a step of bonding the resin lid member 7 to the thermoplastic resin layer 14 by the thermal laminating method, and a step of bonding the dissolution liquid storage container 5 to the lid member 7.

First, the electrode layer 2 is formed on the base member 1 of a PET film or the like to form the electrode film, and a sealing layer 11 is formed on the peripheral portion of the dissolution liquid passage hole 9 formed region on the electrode layer 2 [FIG. 9(a)].

Then, the thermoplastic resin layer 14 is laminated on the entire surface of the base member 1 side of the electrode film, and the dissolution liquid passage hole 9 is formed by punching fabrication [FIG. 9(b)].

As the laminating method of the thermoplastic resin layer 14, various fabrication methods such as an extrusion laminating method, a dry laminating method, a thermal laminating method and the like can be used. The extrusion laminating method extrudes the thermoplastic resin by a T die to laminate, and the dry and thermal laminating method forms a film by an inflation method or a T-die method and laminates it.

Then, the resin lid member 7 is bonded to the thermoplastic resin layer 14 by the thermal laminating method to obtain a lid member-laminated electrode film [FIG. 9(c)].

The drug impregnation member 3 and the expanded sheet 4 are positioned on the sealing layer 11 which is formed on the electrode layer 2 surface of the lid member-laminated electrode film, and they were bonded by heat sealing. Then, the flange portion 5a of the dissolution liquid storage container 5 into which the dissolution liquid 6 is charged is bonded to the lid member 7 surface of the lid member-laminated electrode film to complete the iontophoresis device of the present invention [FIG. 9(d)]. As this bonding method, various types of methods such as heat sealing, impulse sealing, ultrasonic sealing, high-frequency sealing and the like can be used.

In this embodiment, since the dissolution liquid passage hole 9 is formed after the thermoplastic resin layer 14 is formed on the electrode film which is comprised of the base member 1 and the electrode layer 2, there is no thermoplastic resin layer 14 at the region of the dissolution liquid passage hole 9. Therefore, when the lid member 7 is broken at the time of use, the thermoplastic resin layer 14 does not affect on piercing strength, and the dissolution liquid 6 and the drug can be mixed easily.

Manufacturing Example 2

The thermoplastic resin layer 14 was laminated on the base member 1 side in the manufacturing example 1, but this example 2 is an example of laminating the thermoplastic resin layer 14 on the lid member 7 side. FIG. 10 shows its manufacturing process chart.

The manufacturing method of this example has a step of forming the dissolution liquid passage hole 9 in the electrode film, a step of laminating the thermoplastic resin layer 14 on the lid member 7, a step of bonding the lid member 7 to the base member 1 via the thermoplastic resin layer 14 according to the thermal laminating method to cover the dissolution liquid passage hole 9, and a step of bonding the dissolution liquid storage container 5 to the lid member 7.

First, the electrode layer 2 is formed on the base member 1 of a PET film or the like to form the electrode film, the sealing layer 11 is formed on a peripheral portion of the dissolution liquid passage hole 9 formed region on the electrode layer 2, and the dissolution liquid passage hole 9 is formed by punching fabrication [FIG. 10(a)].

The thermoplastic resin layer 14 is laminated on the resin lid member 7 [FIG. 10(b)].

Then, the lid member 7 is bonded to the base member 1 via the thermoplastic resin layer 14 to cover the dissolution liquid passage hole 9 according to the thermal laminating method to obtain a lid member-laminated electrode film [FIG. 10(c)].

The drug impregnation member 3 and the expanded sheet 4 are positioned on the sealing layer 11 which is formed on the electrode layer 2 surface of the lid member-laminated electrode film, and bonded by heat sealing. Then, the flange portion 5a of the dissolution liquid storage container 5 into which the dissolution liquid 6 is charged is bonded to the lid member 7 surface of the lid member-laminated electrode film to complete an iontophoresis device of the present invention [FIG. 10(d)].

In a case where the thermoplastic resin layer 14 is laminated on the resin lid member 7 side as in this example, and especially when a thermoplastic resin which considerably affects on piercing strength is used, the region of the dissolution liquid passage hole 9 is determined to have only the lid member 7 having a single layer structure, so that it is desirable to form the thermoplastic resin layer 14 by using a resin film having an opening corresponding to the dissolution liquid passage hole 9.

Manufacturing Example 3

The resin lid member 7 was bonded to the base member 1 via the thermoplastic resin layer 14 in the manufacturing examples 1 and 2, but this example 3 is an example of bonding the resin lid member 7 to the base member 1 via the adhesive layer 10, and FIG. 11 shows its manufacturing process chart.

The manufacturing method of this example has a step of forming the adhesive layer 10 on only a part of the electrode film to which the dissolution liquid storage container 5 is bonded, a step of forming the dissolution liquid passage hole 9 in an inside region of the electrode film to which the adhesive layer 10 was formed, a step of bonding the resin lid member 7 to the dissolution liquid storage container 5, and a step of bonding the lid member 7 which is bonded to the dissolution liquid storage container 5 to the base member 1 via the adhesive layer 10 to cover the dissolution liquid passage hole 9.

First, the electrode layer 2 is formed on the base member 1 of a PET film or the like to form the electrode film, the sealing layer 11 is formed on a peripheral portion of the dissolution liquid passage hole 9 which is formed in the electrode layer 2, the adhesive layer 10 is coated on only a bonding portion of the base member 1 of the electrode film on the side of the flange portion 5a of the dissolution liquid storage container 5, and the dissolution liquid passage hole 9 is formed by punching fabrication [FIG. 11(a)].

As the adhesive coating method described above, there can be used various coating methods such as gravure coating, reverse coating, lip coating, die coating, comma coating, knife coating, screen printing, calendar coating, hot melt-coating and the like.

The resin lid member 7 is bonded to the flange 5a of the dissolution liquid storage container 5 in which the dissolution liquid 6 is charged [FIG. 11(b)].

Then, the drug impregnation member 3 and the expanded sheet 4 are provided on the sealing layer 11 which is formed on the electrode layer 2 surface of the electrode film, and bonded by heat sealing. The resin lid member 7 to which the flange portion 5a of the dissolution liquid storage container 5 is bonded is bonded to the adhesive layer 10 formed side of the electrode film to complete the iontophoresis device [FIG. 11(c)].

Since the dissolution liquid passage hole 9 is formed after the adhesive layer 10 is formed on the base member 1 side of the electrode film in this example, the region of the dissolution liquid passage hole 9 is free from the adhesive layer 10. Therefore, when the resin lid member 7 is broken at the time of use, the adhesive layer 10 does not affect on piercing strength, and the dissolution liquid and the drug can be mixed easily.

This manufacturing example is preferably applied when the aluminum lid member is used as the lid member 7. Specifically, the aluminum lid member 7 having a sealant layer previously formed on its one side surface is used instead of the resin lid member 7, and the flange portion 5a of the dissolution liquid storage container 5 may be bonded to the lid member 7 with the sealant layer between them.

Manufacturing Example 4

The adhesive layer 10 was formed on the base member 1 side in the manufacturing example 3, but this example 4 is an example of forming the adhesive layer 10 on the lid member 7 side, and its manufacturing process chart is shown in FIG. 12.

The manufacturing method of this example has a step of forming the dissolution liquid passage hole 9 in the electrode film, a step of bonding one side surface of the resin lid member 7 having the adhesive layer 10 formed on the other side surface to the dissolution liquid storage container 5, and a step of bonding the resin lid member 7 which is bonded to the dissolution liquid storage container 5 to the base member 1 with the adhesive layer 10 between them to cover the dissolution liquid passage hole 9.

First, the electrode layer 2 is formed on the base member 1 of a PET film or the like to form the electrode film, the sealing layer 11 is formed on a peripheral portion of the dissolution liquid passage hole 9 on the electrode layer 2, and the dissolution liquid passage hole 9 is formed by punching fabrication [FIG. 12(a)].

The adhesive layer 10 is formed on a release surface of the release film 12, and the resin lid member 7 is laminated on the adhesive layer 10 formed side to obtain an adhesive layer-formed resin lid member [FIG. 12(b)].

Then, the adhesive layer-formed resin lid member 7 is bonded to the flange portion 5a of the dissolution liquid storage container 5 in which the dissolution liquid 6 is charged [FIG. 12(c)].

The drug impregnation member 3 and the expanded sheet 4 are provided on the sealing layer 11 which is formed on the electrode layer 2 surface of the electrode film and bonded by heat sealing. The release film 12 of the adhesive layer-formed resin lid member applied to the flange portion 5a of the dissolution liquid storage container 5 is removed, the lid member 7 is bonded to the base member 1 of the electrode film with the adhesive layer 10 between them to cover the dissolution liquid passage hole 9 with the resin lid member 7 to complete the iontophoresis device [FIG. 12(d)]

In a case where the adhesive layer 10 is coated on the lid member 7 side as in this example, and especially when an adhesive which considerably affects on piercing strength is used, the region of the dissolution liquid passage hole 9 is determined to have only the lid member 7 having single layer structure, so that it is desirable to coat the adhesive by partial coating.

This manufacturing example is preferably applied when an aluminum lid member is used as the lid member 7. Specifically, the aluminum lid member 7 having a sealant layer previously formed on its one side surface is used instead of the resin lid member 7, and the flange portion 5a of the dissolution liquid storage container 5 may be bonded to the lid member 7 with the sealant layer between them.

Manufacturing Example 5

FIG. 13 shows a manufacturing process chart of the iontophoresis device having the structure exemplified in FIG. 8.

The manufacturing method of this example has a step of forming the adhesive layer 10 on only a part of the electrode film to which the dissolution liquid storage container 5 is bonded, a step of forming the dissolution liquid passage hole 9 in a region of the inner side of the electrode film where the adhesive layer 10 is formed, a step of bonding the aluminum lid member 7 having a sealant layer on one side surface to the adhesive layer 10, and a step of bonding the aluminum lid member 7 to the flange portion 5a of the dissolution liquid storage container 5 with the sealant layer between them and arranging the aluminum lid member 7 within the outer diameter of the flange portion 5a of the dissolution liquid storage container 5.

First, the electrode layer 2 is formed on the base member 1 of a PET film or the like to form the electrode film, and the sealing layer 11 is formed on a peripheral portion of the dissolution liquid passage hole 9 on the electrode layer 2 [FIG. 13(a)].

The adhesive layer 10 is coated on a bonding portion of the base member 1 to the flange portion 5a of the dissolution liquid storage container 5, and the dissolution liquid passage hole 9 is formed by punching fabrication in an inside region where the adhesive layer 10 is formed [FIG. 13(b)].

As the adhesive coating method described above, there can be used various coating methods such as gravure coating, reverse coating, lip coating, die coating, comma coating, knife coating, screen printing, calendar coating, hot melt coating and the like.

Then, the aluminum lid member 7 which has a sealant layer formed on its one side in advance is laminated on the adhesive layer 10 formed side of the electrode film, a half-cut line is formed in the lid member 7 along the bonded portion with the flange portion 5a of the dissolution liquid storage container 5, and a portion of the lid member 7 which is not in contact with the adhesive layer 10 is removed. Thus, the lid member-laminated electrode film which has the aluminum lid member 7 bonded to only the portion forming the adhesive layer 10 can be obtained [FIG. 13(c)].

According to the present invention, the aluminum lid member 7 is arranged within only the outer diameter of the flange portion 5a of the dissolution liquid storage container 5, so that the adhesive layer 10 is not formed on the entire surface of the device but only on the bonded portion. Therefore, to form the adhesive layer 10 on the electrode film side, the adhesive layer 10 is formed by the method of partial coating on the bonded portion only as in this embodiment or a method (manufacturing example 6 described later) of laminating a mask film which is coated on the entire surface and has a hole formed in the bonded portion only. Subsequently, lamination with the aluminum lid member 7 causes bonding with only the portion where the adhesive layer 10 is formed, so that when a half-cut line is formed in the aluminum lid member 7 along the bonded portion, the aluminum lid member 7 remains on only the bonded portion as described above, and the portion of the lid member 7 which is not in contact with the adhesive layer 10 can be removed easily.

The drug impregnation member 3 and the expanded sheet 4 are provided on the sealing layer 11 which is formed on the electrode layer 2 surface of the lid member-laminated electrode film and bonded by heat sealing.

Then, the flange portion 5a of the dissolution liquid storage container 5, in which the dissolution liquid 6 is charged, is bonded to the lid member 7 surface of the lid member-laminated electrode film by sealing to complete the iontophoresis device of the present invention having the aluminum lid member 7 arranged within the outer diameter of the flange portion 5a of the blister container 5 [FIG. 13(d)]. The method of sealing the flange portion 5a of the dissolution liquid storage container 5 to the aluminum lid member 7 surface is not particularly limited, but various types of methods such as heat sealing, impulse sealing, ultrasonic sealing, high-frequency sealing and the like can be used.

Manufacturing Example 6

In the manufacturing example 5, the adhesive layer 10 was formed on only the portion of bonding the electrode film to the dissolution liquid storage container 5, but this example 6 is an example of forming the adhesive layer 10 on the entire surface of the electrode film on the side to which the dissolution liquid storage container 5 is bonded, and FIG. 14 shows its manufacturing process chart.

The manufacturing method of this example has a step of forming the adhesive layer 10 on the entire surface of the electrode film on the side to which the dissolution liquid storage container 5 is bonded, a step of forming the dissolution liquid passage hole 9 in the electrode film on which the adhesive layer 10 is formed, a step of laminating the coating film 13 having an opening larger than the dissolution liquid passage hole 9 and the aluminum lid member 7 having a sealant layer on one side surface to the adhesive layer 10 formed side of the electrode film to bond the lid member 7 to the adhesive layer 10 at the opening portion, and a step of bonding the flange portion 5a of the dissolution liquid storage container 5 to the lid member 7 via the sealant layer of the lid member 7 to arrange the aluminum lid member 7 within the outer diameter of the flange portion 5a of the dissolution liquid storage container 5.

First, the electrode layer 2 is formed on the base member 1 such as a PET film to form the electrode film, and the sealing layer 11 is formed on a peripheral portion of the dissolution liquid passage hole 9 formed region on the electrode layer 2 [FIG. 14(a)].

Then, the adhesive layer 10 is coated on the entire surface of the base member 1 side of the electrode film, and the dissolution liquid passage hole 9 is formed by punching fabrication [FIG. 14(b)].

Then, the coating film 13 having an opening which is larger than the dissolution liquid passage hole 9 and smaller than the outer diameter of the flange portion 5a of the dissolution liquid storage container 5 and the aluminum lid member 7 having the sealant layer previously formed on its one side surface are laminated on the adhesive layer 10 formed side of the electrode film. A half-cut line is formed in the lid member 7 along the bonded portion with the flange portion 5a of the dissolution liquid storage container 5, and a portion of the lid member 7 which is not in contact with the adhesive layer 10 is removed. Thus, the lid member-laminated electrode film having the lid member 7 bonded to the adhesive layer 10 at the opening portion of the coating film 13 can be obtained [FIG. 14(c)].

Similar to the manufacturing example 5, the drug impregnation member 3, the expanded sheet 4 and the dissolution liquid storage container 5 are fitted to the lid member-laminated electrode film to complete the iontophoresis device of the present invention having the aluminum lid member 7 arranged within the outer diameter of the flange portion 5a of the dissolution liquid storage container 5 [FIG. 14(d)].

As described above, in the iontophoresis device using the resin lid member, the resin lid member which is used as the lid member of the dissolution liquid storage container is bonded to the electrode film to integrate the dissolution liquid storage container with the electrode film, and since the insulating resin lid member is used as the lid member, the iontophoresis device realized has a structure that the dissolution liquid and the drug can be mixed by a simple operation, and it is free from a possibility of causing a leakage of electricity when current is applied and excellent in reliability and safety.

According to the method for producing the iontophoresis device, the electrode film (or the resin lid member-formed electrode film) can be mass produced by using a material such as a rolled sheet, and the iontophoresis device excelling in reliability and safety can be mass produced easily.

In the iontophoresis device using the aluminum lid member, the aluminum lid member which is used as the lid member of the dissolution liquid container is bonded to the electrode film to integrate the dissolution liquid storage blister container with the electrode film, and since the aluminum lid member is not exposed to the device surface, the iontophoresis device realized has a structure that the dissolution liquid and the drug can be mixed by a simple operation, and it is free from a possibility of causing a leakage of electricity when current is applied and excellent in reliability and safety.

According to the method for producing the iontophoresis device of the present invention, the electrode film (or the aluminum lid member-formed electrode film) can be mass produced by using a material such as a rolled sheet, and especially according to the method of forming the adhesive layer on the entire surface of the electrode film as in the manufacturing example 6, substantially all manufacturing processes of the aluminum lid member-formed electrode film can be performed successively, and the iontophoresis device excelling in reliability and safety can be mass-produced easily.

Examples

The dissolution liquid storage container 5 shown in each of FIG. 15 (Example 1), FIG. 16 (Comparative Example 1) and FIG. 17 (Comparative Example 2) was used to produce the iontophoresis device by the manufacturing process of FIG. 9.

Conductive carbon and a conductive silver chloride paste ink were screen printed on a base member 1 of a biaxially stretched polyethylene terephthalate (PET) film having a thickness of 75 µm to form an electrode layer 2 having a thickness of 30 µm. Then, a sealing layer 11 having a thickness of 10 µm was formed by screen printing an ink composed of a thermoplastic saturated copolymer polyester resin on the peripheral portion of the dissolution liquid passage hole 9 forming region on the electrode layer 2 [FIG. 9(a)].

Then, an anchor coating agent (trade name "TAKELAC" produced by Mitsuitakeda-Chemical Co.) was coated on the entire surface of a non-printed surface of the above-described base member 1. Low-density polyethylene (trade name "Suntec LD" produced by ASAHIKASEI CORPORATION) was additionally laminated by the extrusion laminating method to form a thermoplastic resin layer 14, and the dissolution liquid passage hole 9 was formed by punching fabrication [FIG. 9(b)].

The thermoplastic resin layer 14 and the resin lid member 7 (trade name "PP-MONO-PTP" produced by FUJIMORI KOGYO CO., LTD.) were laminated by fusion bonding by the thermal laminating method to form a lid member-laminated electrode film [FIG. 9(c)].

The dissolution liquid storage container 5 shown in each of FIG. 15, FIG. 16 and FIG. 17 was obtained by vacuum molding of a resin sheet for PTP (trade name "PP-MONO-PTP" produced by FUJIMORI KOGYO CO., LTD.).

The expanded sheet 4 (expanded olefin, trade name "Volara" produced by SEKISUI CHEMICAL CO., LTD.) and the drug impregnation member 3 (nonwoven fabric) were positioned on the sealing layer 11 which was formed on the electrode layer 2 of the lid member-laminated electrode film and bonded mutually by heat sealing. Subsequently, the dissolution liquid 6 having the following composition was charged into the dissolution liquid storage container 5, and with the dissolution liquid passage hole 9 of the lid member-laminated electrode film arranged at the center of the dissolution liquid storage container 5, the flange portion 5a of the dissolution liquid storage container 5 was bonded to the lid member 7 surface of the lid member-laminated electrode film by impulse sealing to complete the iontophoresis device [FIG. 9(d)].

Composition of Dissolution Liquid

Propylene glycol (produced by Maruishi Pharmaceutical Co., Ltd.): 2.00 wt %

Concentrated glycerin (produced by Kozakai Pharmaceutical Co., Ltd.): 30.00 wt %

Purified water (produced by Yoshida Pharmaceutical Co., Ltd.): 68.00 wt %

For each of the iontophoresis devices of Example 1, Comparative Example 1 and Comparative Example 2, loads of 1.5 kg and 2.0 kg were applied to press the bottom of the dissolution liquid storage container 5. After one minute, the amount of the dissolution liquid 6 remaining in the container 5 was measured to calculate the migration rate of the dissolution liquid 6 to the drug impregnation member 3. And, operability was also evaluated. Results are shown in Table 1. Criteria for the operability are as follows.

○: Easy to push with a finger, and less failure of making a hole.

Δ: Larger force is required than "○".

TABLE 1

|  | Migration rate (%) | | Operability |
| --- | --- | --- | --- |
|  | Load 1.5 kg | Load 2.0 kg |  |
| Example 1 | 68.5 | 89.1 | ○ |
| Comparative Example 1 | 22.1 | 88.2 | ○ |
| Comparative Example 2 | 47.8 | 90.9 | Δ |

The invention claimed is:

1. A device for a percutaneous absorption preparation, comprising:
   a holder having a dissolution liquid passage hole;
   a drug impregnation member formed on one surface side of the holder; and
   a dissolution liquid storage container provided on the other surface side of the holder; and
   a lid member covering the dissolution liquid passage hole between the holder and the dissolution liquid storage container, wherein
   the dissolution liquid storage container has a bottom, a sidewall, a flange portion and a protrusion, the bottom and the sidewall forming a recessed portion for storing a dissolution liquid, the flange portion extending from the sidewall and being disposed on the holder, and the protrusion formed at the center of the bottom and within the recessed portion so as to face the dissolution liquid passage hole, and
   the sidewall has a vertically folded part.

2. The device for a percutaneous absorption preparation according to claim 1, wherein the protrusion provided at the center of the bottom and within the recessed portion for storing the dissolution liquid of the dissolution liquid storage container has a recessed portion on its tip end for rupturing the lid member.

3. The device for a percutaneous absorption preparation according to claim 2, wherein the protrusion has a top and a bottom on its outer circumference.

4. The device for a percutaneous absorption preparation according to claim 3, wherein the top and the bottom of the protrusion each are provided in plural and arranged symmetrically to one another on the outer circumference of the protrusion.

5. The device for a percutaneous absorption preparation according to claim 1, wherein the holder has an electrode layer formed on a base member, and the base member is bonded to the lid member to form an iontophoresis device.

6. The device for a percutaneous absorption preparation according to claim 5, wherein the lid member is a resin lid member and bonded to the base member with a thermoplastic resin layer or an adhesive layer between them.

7. The device for a percutaneous absorption preparation according to claim 6, wherein a surface of the resin lid member positioned in the dissolution liquid passage hole does not have the thermoplastic resin layer or the adhesive layer.

8. The device for a percutaneous absorption preparation according to claim 5, wherein the lid member is an aluminum lid member, the dissolution liquid storage container has the flange portion on an opening, and the aluminum lid member is arranged within the outer diameter of the flange portion of the dissolution liquid storage container.

9. The device for a percutaneous absorption preparation according to claim 8, wherein the aluminum lid member and the base member are bonded via an adhesive layer.

10. The device for a percutaneous absorption preparation according to claim 9, wherein a surface of the aluminum lid member positioned in the dissolution liquid passage hole does not have the adhesive layer.

11. The device for a percutaneous absorption preparation according to claim 8, wherein the aluminum lid member and the dissolution liquid storage container are bonded via a sealant layer.

12. The device for a percutaneous absorption preparation according to claim 1, wherein the vertically folded part is disposed at a middle part of the sidewall.

13. The device for a percutaneous absorption preparation according to claim 1, wherein the sidewall has the vertically folded part between the bottom and the flange portion.

14. The device for a percutaneous absorption preparation according to claim 1, wherein the vertically folded part is circumferentially disposed at a middle part of the sidewall and between the bottom and the flange portion.

* * * * *